(12) United States Patent
Erdman

(10) Patent No.: US 6,797,858 B2
(45) Date of Patent: Sep. 28, 2004

(54) PADDED ABSORBENT ARTICLE

(75) Inventor: Edward P Erdman, Duluth, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/971,617

(22) Filed: Oct. 9, 2001

(65) Prior Publication Data

US 2003/0069555 A1 Apr. 10, 2003

(51) Int. Cl.$^7$ ............................. A61F 13/15; A61F 13/20
(52) U.S. Cl. ............. 604/369; 604/385.22; 604/385.24; 604/385.3; 604/396
(58) Field of Search ............................. 604/369, 385.22, 604/385.24, 385.3, 385.31, 396, 400–402; 156/496

(56) References Cited

U.S. PATENT DOCUMENTS

| | | | |
|---|---|---|---|
| 3,916,900 A | * 11/1975 | Breyer et al. ............... | 604/365 |
| 4,610,678 A | 9/1986 | Weisman et al. | |
| 4,640,859 A | 2/1987 | Hansen et al. | |
| 4,646,362 A | 3/1987 | Heran et al. | |
| 4,655,760 A | * 4/1987 | Morman et al. ........ | 604/385.26 |
| 4,834,735 A | 5/1989 | Alemany et al. | |
| 4,950,264 A | 8/1990 | Osborn, III | |
| 5,098,423 A | 3/1992 | Pieniak et al. | |
| 5,147,345 A | 9/1992 | Young et al. | |
| 5,268,224 A | 12/1993 | DesMarais et al. | |
| 5,281,207 A | 1/1994 | Chmielewski et al. | |
| 5,292,316 A | 3/1994 | Suzuki | |
| 5,318,554 A | 6/1994 | Young et al. | |
| 5,324,277 A | * 6/1994 | Daugan et al. .............. | 604/369 |
| 5,331,015 A | 7/1994 | DesMarais et al. | |
| 5,352,711 A | 10/1994 | DesMarais | |
| 5,368,584 A | * 11/1994 | Clear et al. ............. | 604/385.29 |
| 5,376,198 A | * 12/1994 | Fahrenkrug et al. ......... | 156/164 |
| 5,389,168 A | * 2/1995 | Litchholt et al. .............. | 156/77 |
| 5,550,167 A | 8/1996 | DesMarais | |
| 5,632,737 A | 5/1997 | Stone et al. | |
| 5,692,939 A | 12/1997 | DesMarais | |
| 5,755,902 A | * 5/1998 | Reynolds ................... | 156/73.1 |
| 5,786,395 A | 7/1998 | Stone et al. | |
| 5,803,920 A | 9/1998 | Gilman | |
| 5,807,368 A | * 9/1998 | Helmer ........................ | 604/373 |
| 5,830,203 A | 11/1998 | Suzuki et al. | |
| 5,846,232 A | * 12/1998 | Serbiak et al. ......... | 604/385.29 |
| 5,851,648 A | 12/1998 | Stone et al. | |
| 5,863,288 A | 1/1999 | Baker | |
| 5,914,084 A | * 6/1999 | Benson et al. ............... | 264/284 |
| 5,921,973 A | * 7/1999 | Newkirk et al. ............ | 604/365 |
| 5,993,432 A | * 11/1999 | Lodge et al. ............. | 604/385.3 |
| 6,099,950 A | 8/2000 | Wang et al. | |
| 6,121,509 A | 9/2000 | Ashraf et al. | |
| 6,171,291 B1 | 1/2001 | Osborn, III et al. | |
| 6,224,961 B1 | 5/2001 | Hsueh et al. | |
| 6,245,401 B1 | * 6/2001 | Ying et al. ..................... | 428/58 |
| 6,340,782 B1 | * 1/2002 | Kling et al. ................. | 604/366 |
| 6,465,073 B1 | * 10/2002 | Morman et al. ............ | 428/103 |

FOREIGN PATENT DOCUMENTS

| | | | | |
|---|---|---|---|---|
| EP | 0198683 | | 10/1986 | |
| EP | 650714 A1 | * | 5/1995 | ........... A61F/13/15 |
| WO | WO 9743994 A1 | * | 11/1997 | ........... A61F/13/15 |
| WO | WO 0018994 A2 | * | 4/2000 | |
| WO | WO 0115645 A1 | * | 3/2001 | |

* cited by examiner

*Primary Examiner*—Karin Reichle
(74) *Attorney, Agent, or Firm*—Hunton & Williams LLP

(57) ABSTRACT

An absorbent article having front and rear regions corresponding to the front and rear of a wearer, respectively, and a crotch region between the front and rear regions. The article generally has a backsheet, a topsheet overlaying the backsheet, and a foam layer disposed between the topsheet and the backsheet. An absorbent core also is located between the topsheet and the backsheet. The foam layer preferably extends from the front region, through the crotch, and into the back region. The foam layer is attached to the article, while in a laterally extended position, in at least one of the front and rear regions thereby elasticizing at least one region.

7 Claims, 3 Drawing Sheets

PADDED ABSORBENT ARTICLE

FIELD OF THE INVENTION

The present invention generally relates to absorbent garments. In particular, it relates to absorbent garments having a foam layer distributed throughout substantially all of the garment.

BACKGROUND OF THE INVENTION

Absorbent garments, such as diapers, adult incontinence products, training pants, and feminine care products, are in widespread use today. For a variety of reasons, there is a need for thinner absorbent garments. For example, such products may be less expensive to produce, provide quicker or more efficient fluid absorption, or be less bulky. Although thin absorbent products may be able to provide these and other benefits, consumers often perceive thinner absorbent products to be less able to absorb fluids and body exudates than thicker absorbent products.

In addition to perceived deficiencies, thin absorbent products may have actual performance problems that make them less desirable. For example, thin absorbent products may be less comfortable than thicker and more padded absorbent products, and may have an unpleasant granular feel. Also, a thin absorbent product's fluid impervious backsheet may be more susceptible to cutting or puncture during manufacture and use if the absorbent material contains sharp or pointed super absorbent particles, because such a products may have less padding between the absorbent particles and the backsheet. Another problem with thin absorbent products is that they may not provide the requisite absorption capacity. Yet another problem with thin absorbent products is that urine, feces, and other exudates may be visible through the backsheet, providing the product with an unpleasant appearance.

It would be desirable to provide an absorbent garment having additional bulk that makes the garment appear to have a greater absorption capacity. It would also be desirable to provide an absorbent garment that provides additional comfort, a protective barrier between the super absorbent particles and the thin fluid impervious backsheet, and additional absorption capacity. It would also be desirable to provide an absorbent garment that can contain body exudates without them being visible through the garment. It would further be desirable to provide these benefits using conventional materials and while also providing the garment with an elasticized waist band.

The present invention is designed to overcome the foregoing and other deficiencies of prior art absorbent garments.

SUMMARY OF THE INVENTION

The features of the invention generally may be achieved by an absorbent article having an elastic foam layer. The absorbent article typically has a longitudinal dimension corresponding with the front-to-rear axis of a wearer, and a lateral dimension corresponding to the side-to-side axis of a wearer. The article also can have a topsheet and a backsheet overlaying the topsheet. The topsheet and the backsheet form a front region toward the front a wearer, a rear region longitudinally distal from the front region and towards the back of a wearer, and a crotch region between the front and rear regions. In one embodiment, the front and rear regions of the article are brought together to form a waist-encirclable garment having a waist hole and two leg holes.

An elastic foam layer, which may be an open or closed cell foam, may be located between the topsheet and the backsheet, and can extend from the front region, through the crotch region, and into the rear region. The elastic foam layer may be laterally smaller than each of the garment's front region, rear region and crotch region in those respective regions. In one preferred embodiment, the elastic foam layer is a polymeric material. The elastic foam layer, which may be rectangular when it is not extended and hourglass-shaped when the garment is laterally extended, usually is laterally extended then attached to the article in one or both of the front and rear regions. When the extended portions of the foam layer that are attached to the article contract, they cause the article to contract, thereby creating at least one elastically extendible region in the article.

An absorbent core for absorbing and storing fluids and body exudates is located between the topsheet and the backsheet, and may be if located between the topsheet and the elastic foam layer. In one exemplary embodiment, the absorbent core is a thin absorbent core.

In one exemplary embodiment, the elastic foam layer inhibits materials in the absorbent core from cutting or puncturing the backsheet. In another exemplary embodiment, the elastic foam layer is opaque enough to prevent urine, feces and other body exudates from being viewed through the backsheet. In a further exemplary embodiment, the elastic foam layer increases the absorbent capacity of the article. In yet another exemplary embodiment, the elastic foam layer increases the cushioning of the article.

DETAILED DESCRIPTION OF THE PREFERRED EMBODIMENTS

As used herein, the terms "absorbent garment," "absorbent article" or simply "article" or "garment" refer to devices that absorb and contain body fluids and other body exudates. More specifically, these terms refer to garments that are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present invention may be used with all of the foregoing classes of absorbent garments, without limitation, whether disposable or otherwise. The embodiments described herein provide, as an exemplary structure, a diaper for an infant, however this is not intended to limit the claimed invention. The invention will be understood to encompass, without limitation, all classes and types of absorbent garments, including those described herein.

For clarity, features that appear in more than one Figure have the same reference number in each Figure.

Figure 1:
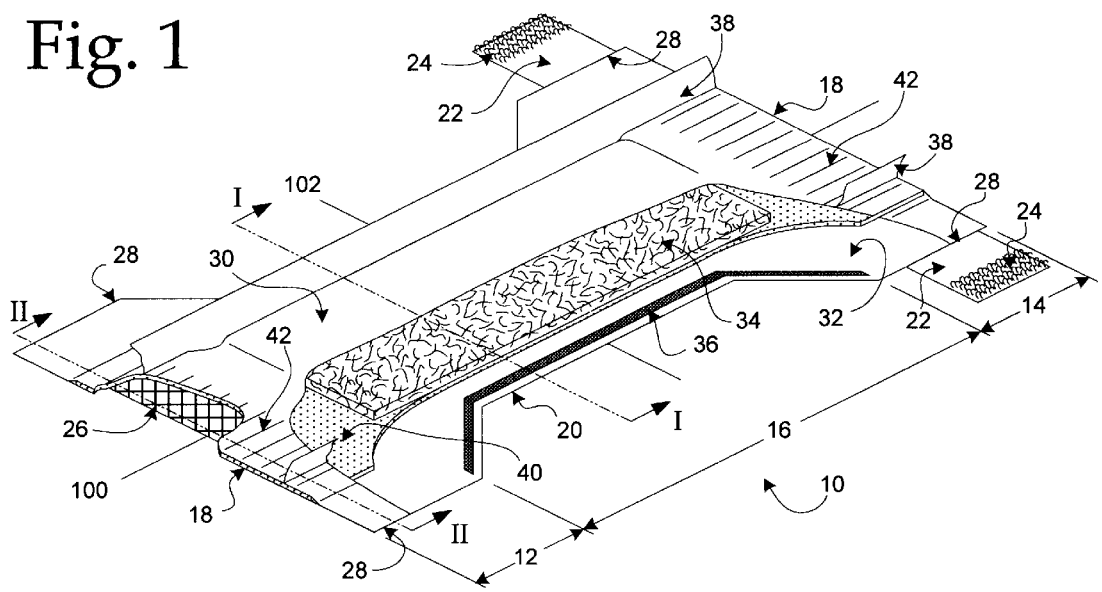
FIG. 1 is a partially cut-away view of an embodiment of the present invention, shown in the fully-flattened position.

FIG. 1 is a partially cut away depiction of an exemplary embodiment of a garment 10 of the present invention. The embodiment shown in FIG. 1 is an infant's diaper, however, this depiction is not intended to limit the invention. The garment 10 of FIG. 1 is depicted in a flattened position, with the various elastic components depicted in their extended position for clarity. In the flattened position, the garment 10 generally has an hourglass shaped structure, but it may also have a rectangular, trapezoidal or other shape.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, an embodiment of the invention may comprise a pant-like garment 10 having a waist-encircling region and a crotch region. The waist-encircling region may comprise a front region 12, corresponding with the front of a wearer's body, and a rear region 14, corresponding with the back of a wearer's body, that are joined together at or near their lateral edges 28, causing the longitudinally distal edges 18 of the garment 10 to form the perimeter of a waist opening. The crotch region 16 extends between the front and rear regions 12, 14, and the crotch edges 20 form the perimeter of a pair of leg openings.

The front and rear regions 12, 14 may be joined to one another by permanent seams (not shown) or by releasable fasteners 22. The releasable fasteners 22 may comprise an adhesive tape, a mechanically interlocking fastener, such as a hook and loop fastener 24 or a button or snap, or any other suitable releasable fastening device. The garment may also comprise a target surface 26 associated with a surface of the garment 10, that is selected to interact with the releasable fasteners 22 to provide them with the grip necessary to hold the garment 10 together. While the embodiment depicted in FIG. 1 shows the releasable fasteners 22 being located in the rear region 14, and the target surface 26 being in the front region 12, skilled artisans will recognize that these locations may be reversed. The selection and manufacture of permanent side seams, releasable fasteners 22, and target surfaces 26 is known in the art, and a skilled artisan will be able to implement such structures and devices without undue experimentation.

The garment 10 preferably comprises a topsheet 30, and a backsheet 32, which may be substantially coterminous with the topsheet 30. When the garment 10 is being worn, the topsheet 30 faces the wearer's body, and the backsheet 32 faces away from the wearer. A foam layer 40 preferably is located between the topsheet 30 and the backsheet 32. The foam layer 40 may extend from the front region 12, through the crotch region 16, and into the rear region 14, and may be attached to the garment 10 in at least one of the front region 12 and the rear region 14. It is particularly preferred in the invention that at least one longitudinal end of the foam layer 40 be extended prior to being attached to the garment 10, such that when the foam layer 40 contracts it causes the garment to shirr or gather.

Figure 2:
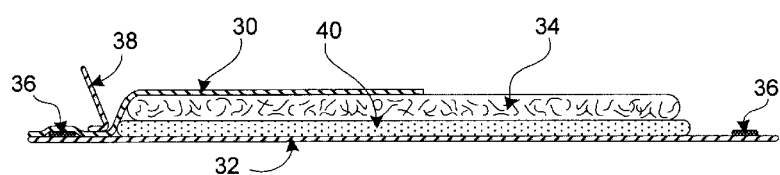
FIG. 2 is a cross-sectional view of the embodiment of FIG. 1, as viewed from reference line I—I.

An absorbent core 34 usually is disposed between at least a portion of the topsheet 30 and foam layer 40, or between the foam layer 40 and at least a portion of the backsheet 32. Preferably, the absorbent core 34 is disposed between at least a portion of the topsheet 30 and foam layer 40. The preferred relative positions of the topsheet 30, backsheet 32, absorbent core 34 and foam layer 40 may be seen in FIG. 2, which is a cross-sectional view of the garment 10 of FIG. 1 as seen from reference line I—I.

An embodiment of the present invention may further comprise various additional features. One or more pairs of leg elastics 36 may extend adjacent the crotch edges 20. The garment 10 may also comprise one or more waste containment systems, such as a pair of standing leg gathers 38. The standing leg gathers 38 preferably extend longitudinally between the front region 12 and the rear region 14 along opposite sides of the garment's longitudinal axis 100.

The various parts of the garment 10 are associated with one another to form a structure that preferably maintains its shape during the useful life of the garment 10. As used herein, the term "associated" encompasses configurations whereby a first part is directly joined to a second part by affixing the first part directly to the second part, by indirectly joining the first part to the second part through intermediate members, or by fixing the relative positions of various parts by capturing parts between other parts. Those skilled in the art will appreciate that various methods or combinations of methods may be used to securely join the parts of the garment 10.

These features, and other features, functions and uses of the present invention, are described in greater detail herein.

The topsheet 30 and backsheet 32 may be constructed from a wide variety of materials known in the art. The invention is not intended to be limited to any specific materials for these components. The topsheet 30 and backsheet 32 may be shaped and sized according to the requirements of each of the various types of absorbent garment, or to accommodate various user sizes. In an embodiment of the invention in which the garment 10 is a diaper or an adult incontinence brief, the topsheet 30, backsheet 32, or both, may have an hourglass shape, as seen in FIG. 1, or may have a rectangular, trapezoidal, "T" shape, or other shape. In an embodiment of the invention in which the garment 10 is a feminine hygiene product, the topsheet 30, backsheet 32, or both, may have a rectangular or ovate shape, and may have tabs or "wings."

The backsheet 32 generally is made of any suitable pliable liquid impervious material known in the art or later discovered. Typical backsheet materials include films of polyethylene, polypropylene, polyester, nylon, and polyvinyl chloride and blends of these materials. For example, the backsheet 32 may be made of a polyethylene film having a thickness in the range of 0.02–0.04 mm. The backsheet 32 may be pigmented with, for example, titanium dioxide, to provide the garment 10 with a pleasing color or to render the backsheet 32 opaque enough that exudates being contained by the garment 10 are not visible from outside the garment. In addition, backsheet 32 may be formed in such a manner that it is opaque, for example, by using various inert components in the polymeric film and then biaxially stretching the film. Other backsheet materials will be readily apparent to those skilled in the art. The backsheet 32 preferably should have sufficient liquid imperviousness to prevent any leakage of fluids through the backsheet 32. The required level of liquid imperviousness may vary between different locations on the garment 10.

The backsheet 32 may further comprise separate regions having different properties. In a preferred embodiment, portions of the backsheet 32 are air-permeable to improve the breathability, and therefore comfort, of the garment 10. The different regions may be formed by making the backsheet 32 a composite of different sheet materials, chemical treatment, heat treatment, or other processes or methods known in the art. Some regions of the backsheet 32 may be fluid pervious. In one embodiment of the invention, the backsheet 32 is fluid impervious in the crotch 12, but is fluid pervious in portions of the front and rear regions 12, 14. The backsheet 32 may also be made from a laminate of overlaid sheets of material.

The backsheet 32 may be covered with a fibrous, non-woven fabric such as is disclosed, for example, in U.S. Pat. No. 4,646,362 issued to Heran et al., which is hereby incorporated by reference in its entirety and in a manner consistent with the present application and invention. Materials for such a fibrous outer liner include a spun-bonded nonwoven web of synthetic fibers; a nonwoven web of cellulosic fibers, textile fibers, or a blend of cellulosic and textile fibers; a spun-bonded nonwoven web of synthetic fibers mixed with cellulosic, pulp fibers, or textile fibers; and melt blown thermoplastic fibers or mixtures of such thermoplastic fibers with cellulosic, pulp or textile fibers.

The moisture-pervious topsheet 30 may be made of any suitable relatively liquid-pervious material currently known in the art or later discovered that permits passage of a liquid therethrough. Examples of suitable topsheet materials include nonwoven spun-bonded or carded webs of polypropylene, polyethylene, nylon, polyester and blends of these materials, perforated, apertured, or reticulated films, and the like. Nonwoven materials are exemplary because such materials readily allow the passage of liquids to the underlying absorbent core 34. The topsheet 30 preferably comprises a single-ply nonwoven material that may be made of carded fibers, either adhesively or thermally bonded, perforated or apertured film, spunbonded fibers, or water entangled fibers, which generally weigh from 0.3–0.7 oz./sq. yd. and have appropriate and effective machine direction and cross-machine (transverse) direction strength suitable for use as a topsheet material for the given application. The present invention is not intended to be limited to any particular material for the topsheet 30, and other topsheet materials will be readily apparent to those skilled in the art.

The topsheet 30 may further comprise several regions having different properties. In one embodiment of the present invention, the laterally distal portions of the topsheet 30 are preferably substantially fluid impervious and hydrophobic, while the remainder of the topsheet 30 is hydrophilic and fluid pervious. Different topsheet properties, such as fluid perviousness and hydrophobicity, may be imparted upon the topsheet 30 by treating the topsheet 30 with adhesives, surfactants, or other chemicals, using a composite of different materials, or by other means. The topsheet 30 may also be made from a laminate of overlaid sheets of material. The topsheet 30 also may be treated in specific areas like the crotch region, with skin wellness ingredients like aloe and vitamin E.

As noted elsewhere herein, the topsheet 30 and backsheet 32 may be substantially coterminous, or they may have different shapes and sizes. The particular design of the topsheet and backsheet may be dictated by manufacturing considerations, cost considerations, and performance considerations. Preferably, the topsheet 30 is large enough to completely cover the absorbent core 34, and the backsheet 32 is large enough to prevent leakage from the garment 10. The design of topsheets 30 and backsheets 32 is known in the art, and a skilled artisan will be able to produce an appropriate topsheet 30 and an appropriate backsheet 32 without undue experimentation.

The topsheet 30 and the backsheet 32 may be associated with one another using a variety of methods known in the art. For example, they may be thermally, ultrasonically, or chemically bonded to one another. They also may be joined using lines of hot melt adhesive or mechanical fasteners, such as thread, clips, or staples. In one embodiment, a hydrophilic adhesive, such as those sold by National Starch and Chemical Company of Bridgewater, N.J. under the trademark CYCLOFLEX, is used to join the topsheet 30 to the backsheet 32. The particular joining method may be dictated by the types of materials selected for the topsheet 30 and backsheet 32.

An absorbent core 34 preferably is disposed between the topsheet 30 and the foam layer 40 in at least the crotch region 16. The absorbent core 34 may extend into either or both of the front and rear regions 12, 14. Although the absorbent core 34 depicted in FIG. 1 has a substantially rectangular shape, other shapes may be used, such as a "T" shape or an hourglass shape. The shape of the absorbent core 34 may be selected to provide the greatest absorbency with a reduced amount of material. The absorbent core may be associated with the topsheet 30, backsheet 32, or any other suitable part of the garment 10 by any method known in the art, in order to fix the absorbent core 34 in place.

The absorbent core 34 may be made from any suitable material or materials known in the art. Examples of suitable materials for use as the absorbent core 34 include creped cellulose wadding, absorbent foams, absorbent sponges, super absorbent polymers, absorbent gelling materials, fiberized cellulose, fluff pulp having tissue or synthetic materials between the absorbent core 34 and the topsheet 30 or any equivalent material or combination of materials. The size and capacity of the absorbent material should correspond to the application, for example, an incontinent brief for an adult may require a larger absorbent core than a diaper for a child. Zoned absorbency may also be used, if desired. For example, more absorbent capacity may be located in particular regions of the garment 10 depending on the gender of the intended wearer. The invention is not intended to be limited to any specific materials for use in the absorbent core 34.

In a preferred embodiment, the absorbent core 34 comprises super absorbent polymer distributed within a fibrous structure. Absorbent cores of this type are known in the art, and exemplary absorbent cores are described in U.S. Pat. No. 5,281,207, issued to Chmielewski et al., and U.S. Pat. No. 5,863,288, issued to Baker, which are herein incorporated by reference in their entirety.

Additional sublayers, transfer layers, acquisition layers, tissue wraps, and the like also may be incorporated into the absorbent core 34. Such layers may be provided to assist with transferring fluids to the absorbent core 34, handling fluid surges, preventing rewet, containing absorbent material, improving core stability, or for other purposes. For example, a substantially rectangular, preferably nonwoven, sublayer (not shown), having a basis weight of about 0.1–2 oz., preferably about 0.4–0.6 oz., may overlay absorbent core 34. Those skilled in the art are capable of selecting materials, dimensions, and locations for such layers without undue experimentation.

A foam layer 40 preferably is disposed between the topsheet 30 and the backsheet 32. The foam layer preferably extends from the front region 12, through the crotch 16, and into the rear region 14. It is preferred that the foam layer 40 be approximately the same width as, or wider than, the absorbent core 34; however, part or all of the absorbent core 34 may be wider than the foam layer 40.

The foam layer 40 may comprise any suitable elastic foam material, such as polyurethane, polymeric foams such as dienes, polymers made from water-in-oil emulsions (e.g., high internal phase emulsions (HIPE)), and the like. There are myriad documents describing suitable foams for use in an absorbent article, and the present invention is not intended to be limited to any particular type of foam material. Suitable foam materials are described in, for example, U.S. Pat. Nos. 5,147,345, 5,268,224, 5,318,554, 5,331,015, 5,352,711, 5,550,167, 5,632,737, 5,692,939, 5,786,395, and 5,851,648, the disclosure of each of which is incorporated by reference herein in its entirety, and in a manner consistent with this disclosure.

The foam layer 40 may comprise an open cell or closed cell structure. The foam layer 40 preferably extends to the longitudinally distal edges 18 of the garment 10. In such an embodiment, the portions of the foam layer 40 proximal to the longitudinally distal edges 18 may improve the fit, comfort, and leakage resistance of such articles. These portions of the foam layer 40 may also reduce the likelihood that the edge of the garment will double over on itself, or "roll over," by providing rigidity to the edge of the garment.

In a preferred embodiment, the foam layer 40 is associated with the garment 10 in the front and rear regions 12, 14, such the garment 10 tends to contract around the wearer's body when the foam layer 40 elastically contracts. Preferably, the foam layer 40 provides a lateral contracting force to the front and rear regions 12, 14, but not to the crotch region 16. In one embodiment, the portions of the foam layer 40 in both the front and rear regions 12, 14 are stretched along the lateral axis 102 prior to being associated with the garment 10. In this embodiment, the foam layer 40 then is attached to the garment 10 in the front and rear regions 12, 14 in this extended state. Preferably, the foam layer 40 is attached to one or both of the topsheet 30 and the backsheet 32, however, the foam layer 40 may be attached to any suitable part of the garment 10 located in the front and rear regions 12, 14. When the foam layer 40 is allowed to contract, the restoring force contracts the garment 10 around a wearer's waist. The portion of the foam layer that resides in the crotch region 16 preferably is not directly joined to the garment 10, or is joined to the garment 10 while it is contracted, so that this part of the foam layer 40 is in a relaxed or contracted state during use. In another embodiment, the foam layer 40 may comprise a heat-activated elastic material that is attached to the garment 10 in the relaxed state, then heat activated to cause it to elastically contract. Such a materials is disclosed in U.S. Pat. No. 4,640,859, issued to Hansen et al., the disclosure of which is incorporated herein by reference in its entirety.

In one embodiment, that may be appropriate as an infant's diaper, the foam layer is between about 3 inches and about 6 inches wide ("width" being measured in the lateral dimension 102). In this embodiment, the longitudinal ends of the foam layer 40 may be stretched along the lateral axis 102 to about 105% to about 200% of their original width before being secured to the garment 10. More preferably, the longitudinal ends of the foam layer 40 may be stretched along the lateral axis 102 to be about 110% to about 175% of their original width before being secured to the garment 10. Most preferably, the longitudinal ends of the foam layer 40 may be stretched along the lateral axis 102 to about 130% to about 140% of their original width before being secured to the garment 10.

Wider garments 10, such as those intended for use by adults, may benefit from a wider foam layer 40. In addition, the foam layer 40 may be provided with a greater or lesser amount of stretch prior to being secured to the garment 10, depending on whether the application requires a greater or lesser contracting force, respectively. Those skilled in the art are capable of stretching the various portions of foam layer 40, and using various sizes and types of foam layer 40, using the guidelines provided herein.

Figure 5:
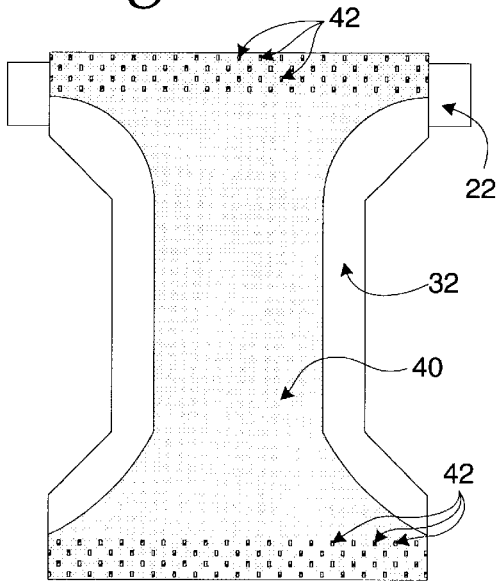
FIG. 5 is a planar view of an embodiment of the present invention in which the foam layer extends to the laterally distal edges of the topsheet, shown with the topsheet removed for clarity and the foam layer in the elastically extended position.

Generally, the foam layer 40 is narrower than the topsheet 30 and backsheet 32 so that the foam layer is fully contained between the topsheet 30 and backsheet 32. The width of the foam layer 40 in the crotch region 16 may be established so that the foam layer does not cause bunching of the garment between the wearer's legs, and does not increase the rigidity of the crotch edges 20, which may cause discomfort and leakage. The width of the foam layer 40 in the front and rear regions 12, 14 may be selected to provide improved fit, comfort and leakage protection. In one embodiment, the foam layer 40 may extend to the lateral edges 28 of the topsheet 30 or backsheet 32 in one or both of the front and rear regions 12, 14, as depicted in FIG. 5.

The foam layer 40 may be attached to the garment 10 by any suitable method known in the art. Exemplary bonding methods include using hot melt adhesives, ultrasonic bonding, heat welding, chemical bonding, and the like. As the number and size of the bonds increase, the elasticity of the foam layer 40 may decrease due to the increased rigidity of the bond areas. This stiffening effect may be reduced by using flexible adhesives to bond the foam layer 40 to the garment. The shape and orientation of the bonds may also impact the overall stiffness of the foam layer 40.

Figure 3A:
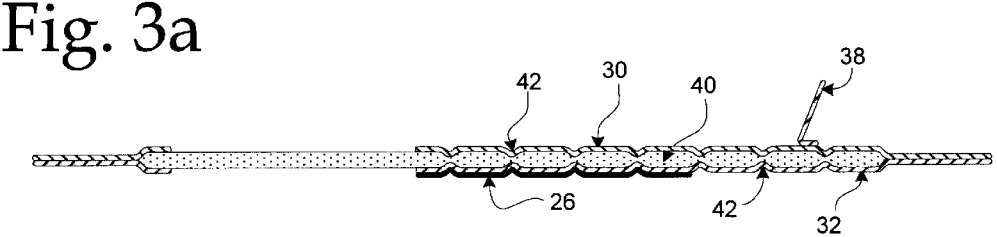
FIG. 3a is a cross-sectional view of the embodiment of FIG. 1, as viewed from reference line II—II with the garment in the elastically extended position.
Figure 3B:
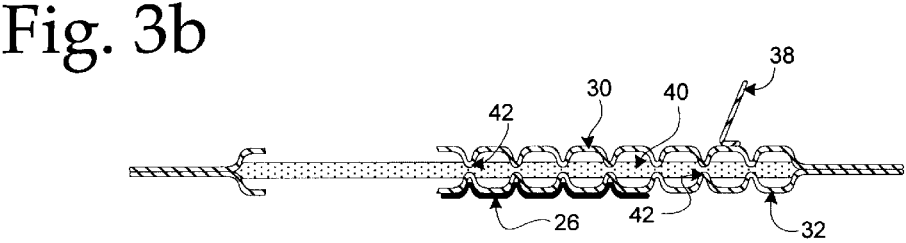
FIG. 3b is a cross-sectional view of the embodiment of FIG. 1, as viewed from reference line II—II with the garment in the elastically contracted position.
Figure 4A:
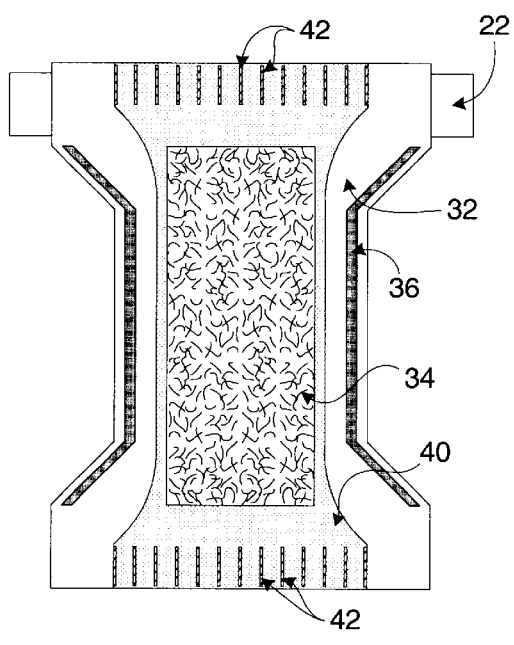
FIG. 4a is a planar view of an embodiment of the present invention, shown with the topsheet removed for clarity and the foam layer in the elastically extended position.
Figure 4B:
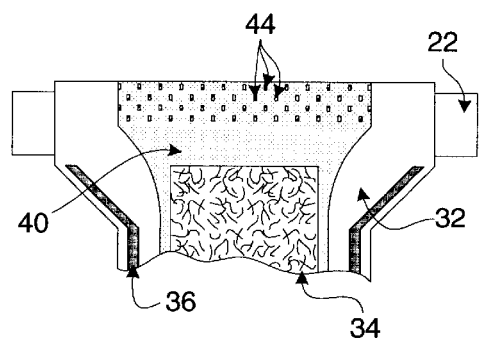
FIG. 4b is a planar cut-away view of another embodiment of the present invention, shown with the topsheet removed for clarity and the foam layer in the elastically extended position.
Figure 4C:
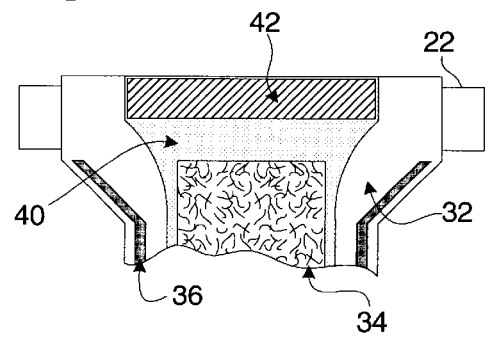
FIG. 4c is a planar cut-away view of yet another embodiment of the present invention, shown with the topsheet removed for clarity and the foam layer in the elastically extended position.

In one embodiment, depicted in FIGS. 1, 2, 3a, 4a, 6, 7 and 8, the foam layer 40 is attached at a plurality of linear attachment points 42. FIGS. 3a and 3b depict cross-sectional views of the garment of FIG. 1 as viewed along reference line II—II FIG. 3a shows the foam layer 40 in an elastically extended position, and FIG. 3b shows the same cross-sectional view with the foam layer 40 in an elastically contracted position. In another embodiment, the foam layer 40 may be attached to the garment 10 using a lattice or matrix pattern of points 44, such as depicted in FIG. 4b. In yet another embodiment, depicted in FIG. 4c, the foam layer 40 is attached to the garment 10 throughout one or more large areas using a relatively elastic bonding material.

Figure 6:
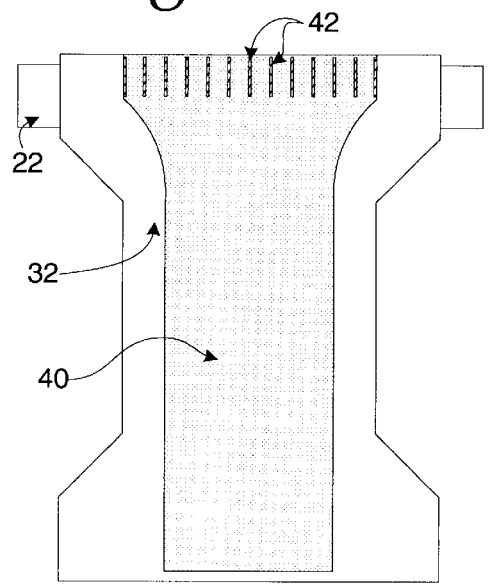
FIG. 6 is a planar view of an embodiment of the present invention in which the foam layer is attached in the extended position only to the rear region of the garment, shown with the topsheet removed for clarity and the foam layer in the elastically extended position.

In the embodiments discussed thus far, the foam layer 40 is joined to the garment 10 in a stretched condition in both the front and rear regions 12, 14. In another embodiment, however, the foam layer 40 may be joined to the garment 10 in only the front region 12 or the rear region 14, as depicted in FIG. 6. The remainder of the foam layer 40 in such an embodiment may be associated with the garment 10 in an unstretched condition (by, for example, directly joining the foam layer 40 to the garment 10 or by capturing it in place) such that the foam layer 40 does not provide a lateral contracting force.

Figure 7:
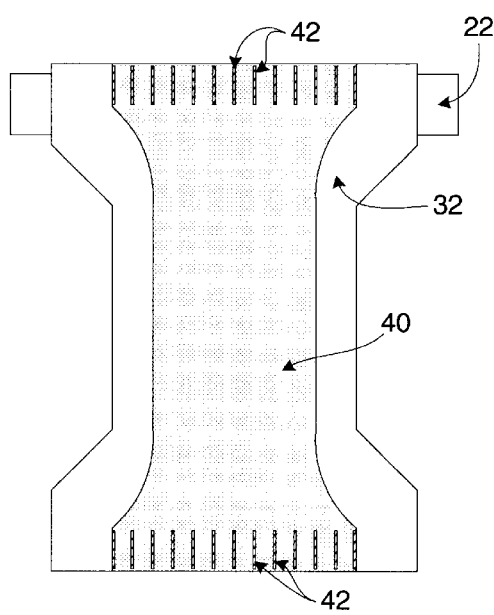
FIG. 7 is a planar view of an embodiment of the present invention in which the foam layer is attached in the extended position to the front and rear regions of the garment, shown with the topsheet and absorbent core removed for clarity and the foam layer in the elastically extended position.
Figure 8:
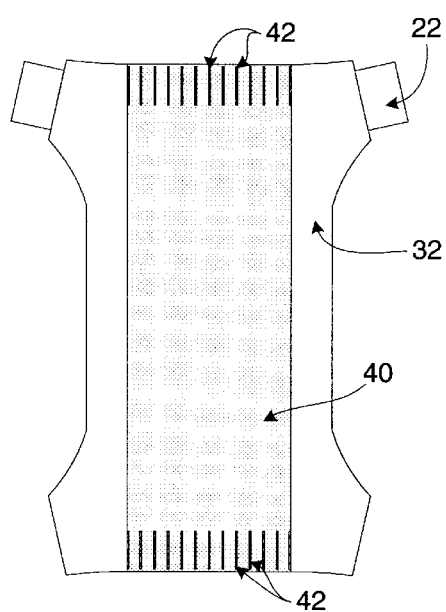
FIG. 8 is a planar view of the embodiment of FIG. 7 shown with the foam layer in the elastically contracted position.

In another embodiment, shown in FIGS. 7 and 8, the elastic foam layer 40 may have a substantially rectangular shape when the garment is in an unextended position, as shown in FIG. 8, and a substantially hourglass-like shape when the garment is in a laterally extended position, as shown in FIG. 7.

The present invention may be utilized to provide a number of benefits, some of which are detailed below. Other uses and benefits will be apparent to those skilled in the art. Some or all of these benefits may be obtained using conventional elastic polyurethane waist foam material, and a cost savings may be obtained by using such a construction.

The present invention may be particularly suited for use with thin absorbent cores 34 (i.e., those that provide relatively high fluid absorbency as compared with their dry volume). Thin absorbent cores 34 typically comprise a relatively high volume of super absorbent material, when compared to the volume of fibrous filler or structure. Consequently, such absorbent cores are relatively thin and lightweight. Thin absorbent cores without the use of superabsorbent materials also may be used in the present inventions. Such thin absorbent materials are disclosed, for example, in U.S. Pat. No. 5,803,920, the disclosure of which is incorporated by reference herein in its entirety. The particular foam materials disclosed in this patent also are useful herein.

The absorbent core 34 may be any absorbent means that is capable of absorbing or retaining liquids (e.g., menses and/or urine). The absorbent core 34 may be manufactured in a wide variety of sizes and shapes (e.g., rectangular, oval, hourglass, dog bone, asymmetric, etc.).

In a preferred embodiment, the absorbent core 34 is a laminate comprised of a layer of superabsorbent polymer material in the form of particles disposed between two air-laid tissues, first and second tissue layers (or "upper" and "lower" tissue layers). The first and second tissue layers contain the superabsorbent polymer material, improve lateral wicking of the absorbed exudates throughout the absorbent core 34 and provide a degree of absorbency.

The absorbent core 34 may, however, be made from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; thermally bonded air-laid fibers; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 34 also may be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 34 should, however, be compatible with the design loading and the intended use of the absorbent article. Further, the size and absorbent capacity of the absorbent core 34 may be varied to accommodate different uses such as incontinence pads, pantiliners, regular sanitary napkins, overnight sanitary napkins, regular diapers, overnight diapers, adult diapers, pull-on pants, etc.

Exemplary absorbent structures for use as the absorbent core of the present invention are described in U.S. Pat. Nos. 4,950,264, 4,610,678, 4,834,735, 6,099,950, 6,121,509, 6,171,291, 6,224,961, and European Patent Application No. 0 198 683, the disclosures of which are incorporated by reference herein in their entirety.

For example, a thin absorbent core may comprise a low bulk compressed fibrous web layer having super absorbent particles distributed therein. Such cores are known in the art, and an exemplary thin core is disclosed in U.S. Pat. No. 5,098,423 issued to Pieniak et al. on Mar. 24, 1992, which is hereby incorporated by reference in its entirety.

Although thin cores generally provide suitable absorbency, it has been found that caregivers often express concern that garments constructed with thin absorbent cores will be inadequate at absorbing fluids and exudates. The foam layer 40 may add visible and tactile thickness to an absorbent garment, thereby increasing the trust of caregivers. The present invention may also increase the absorbent capacity of the garment 10, particularly when the foam layer 40 comprises an open celled foam. A gas pervious open celled foam may also provide additional breathability to a garment, provided that the surrounding materials are similarly gas pervious.

The foam layer 40 may also provide cushioning for the garment's user. Such cushioning may increase user comfort by making the garment 10 softer, and may help prevent injuries, especially in the case of users susceptible to bone injuries, such as some elderly persons. The thickness of the foam layer may be varied to provide cushioning for more sensitive areas of the user's body, such as the tailbone and the hips.

In addition to providing a thicker look and feel, in another embodiment of the invention, the foam layer 40 may be selected to serve as a barrier between the absorbent core 34 and the backsheet 32. Super absorbent materials often are provided in a particulate form. The particles may have a variety of shapes and sizes, and some types of super absorbent materials may have particles with sharp edges or points that can pierce the backsheet 32, thereby causing leakage. The backsheet is particularly susceptible to cuts or piercing during use when the wearer sits on the garment and during manufacture during which the article may be compressed at various points. The present invention preferably provides a physical barrier between the super absorbent particles in the absorbent core 34 and the backsheet 32, and may help to prevent sharp or pointed particles of super absorbent material from damaging the backsheet. This benefit may be even greater in garments having thin absorbent cores, in which case the decreased amount of padding in the form of fibrous structure and filler in the absorbent core 34, and the increased about of super absorbent particles, add to the likelihood of a puncture or cut.

In an embodiment employing the foam layer 40 as a barrier to prevent cuts and punctures, the foam layer 40 preferably comprises material having pore sizes, pore density, thickness, web strength and stiffness such that the super absorbent particles can not extend through the foam layer 40, even when the foam layer 40 is compressed by the weight of the user. Using the guidelines provided herein, a person skilled in the art can design a suitable foam layer 40, having the requisite pore sizes, pore density, thickness, web strength and stiffness to prevent super absorbent particles from extending therethrough.

In yet another embodiment of the invention, the foam layer 40 provides additional opaqueness to the garment 10. Such opaqueness may help prevent urine, feces, and other body exudates from being visible through the backsheet 32. In such an embodiment, the backsheet 32 may not have to be treated or colored to render it more opaque, possibly reducing the cost to produce each garment 10 and the amount of chemical waste produced by the manufacturing process.

The thickness of the foam layer 40 may vary depending on the desire to obtain the benefits described herein or other benefits. The foam layer may have a uniform uncompressed thickness, or it may be constructed with a non-uniform thickness in order to provide localized thicker or thinner regions that may provide specific benefits to particular areas of the garment 10. In one embodiment, the foam layer 40 may have a uniform or varied uncompressed thickness of between about 0.125 millimeters and about 5.000 millimeters. The uncompressed thickness refers to the thickness of the foam layer 40 in its fully relaxed state, prior to being assembled into the garment 10.

The above benefits, and others, may be obtained by employing a properly selected elastic foam layer 40, and thin absorbent core 34. Other materials, such as thin pure pulp layers, airlaid bonded pulp layers, and bulky nonwoven layers, may be used to provide some of the above benefits, but may not provide all of the above benefits. In particular, none of these other materials may be readily used to provide elasticized front and rear regions 12, 14 for the garment 10.

Referring back to FIG. 1, the crotch region 16 may also include mechanical sealing devices to provide the garment 10 with a leak-proof fit around the wearer. In a preferred embodiment, the crotch edges 20 each have one or more elastic gathers 36 placed along them to help the crotch edges 20 contract about the contours of the wearer's body, thereby providing a leak-proof seal. Such gathers 36 are known in the art, and are disclosed, for example, in U.S. Pat. No. 5,830,203, issued to Suzuki et al., which is herein incorporated by reference in its entirety in a manner consistent with the present invention. The gathers 36 may extend into the rear waist band 14, and may extend as far as the front longitudinally distal edge 18.

In another preferred embodiment, a standing leg gathers 38 are disposed on the topsheet 30. Standing leg gathers 38 are strips of material that rise vertically from the surface of the topsheet 30 to provide additional sealing to the garment 10. The standing leg gathers 38 may extend across all or part of the garment 10 along its longitudinal axis 100. Typically, one standing leg gather 38 is located on either side of the absorbent core 34. The standing leg gathers 38 may be made from folded portions of the topsheet 30 or backsheet 32, or may be made from additional strips of material. Each standing leg gather 38 may be equipped with one or more elastic elements to help seal the gather to the wearer's body. Standing leg gathers are known in the art, and disclosed in U.S. Pat. No. 5,292,316, issued to Suzuki, which is herein incorporated by reference in its entirety in a manner consistent with the present invention.

Any suitable elastic material may be used for the gathers 36 and the standing leg gathers 38. Preferably, the elastic material may be stretched to between more than 10% to 300% of its original length without losing its resilience. The elastic material used for the gathers 36 and standing leg gathers 38 may comprise an elastic film, a multidirectional elastic aggregate such as elastic webbing, netting, or scrim elastic, such as FLEXCEL Elastic Nonwoven Laminate, available from Kimberly-Clark Corporation, headquartered in Neenah, Wis., or strands or bands of suitable elastic materials, such as natural or synthetic rubber, urethane elastomers, spandex, LYCRA and elastic polymers. The elastic materials may be attached to the garment 10 in any of several ways known in the art. For example, the elastic materials may be ultrasonically bonded, heat/pressure sealed using a variety of bonding patterns, or glued to the diaper 10 using a variety of adhesives. Other performance enhancing devices, such as pockets, baffles, and openings in the topsheet also may be used with the present invention.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

I claim:

1. An absorbent article having a longitudinal dimension and a lateral dimension comprising:
   a topsheet;
   a backsheet overlaying the topsheet;
   the topsheet and the backsheet forming a front region, a rear region longitudinally distal from the front region, and a crotch region therebetween;
   the front and rear regions being joined to form a waist-encirclable garment having a waist hole and a pair of leg holes;
   an elastic foam layer having a substantially rectangular shape while in an unextended position, disposed between the topsheet and the backsheet and extending from the front region, through the crotch region, and into the rear region;
   the elastic foam layer being laterally smaller than each of the front region, the rear region, and the crotch region in those respective regions;
   the elastic foam layer being attached to the article in the front and rear regions while it is laterally extended, thereby creating elastically extendible regions in the front and rear regions of the article;
   the elastic foam layer being attached to the article in the crotch region while in an elastically contracted state such that the elastic foam layer does not impart elasticity to the article in the crotch region; and
   a thin absorbent core disposed between the topsheet and the elastic foam layer.

2. The absorbent article of claim 1, wherein the elastic foam layer is an open celled foam.

3. The absorbent article of claim 1, wherein the elastic foam layer is a closed celled foam.

4. The absorbent article of claim 1, wherein the elastic foam layer inhibits the absorbent core from cutting the backsheet.

5. The absorbent article of claim 1, wherein the elastic foam layer inhibits the ability to view exudates through the backsheet.

6. The absorbent article of claim 1, wherein the elastic foam layer increases the absorbent capacity of the article.

7. The absorbent article of claim 1, wherein the elastic foam layer increases the cushioning of the article.

* * * * *